US008507452B2

(12) United States Patent
Sono

(10) Patent No.: US 8,507,452 B2
(45) Date of Patent: Aug. 13, 2013

(54) HESPERIDIN-CONTAINING COMPOSITION

(75) Inventor: Ryohei Sono, Takatsuki (JP)

(73) Assignee: Sunstar Inc., Osaka (JP)

(*) Notice: Subject to any disclaimer, the term of this patent is extended or adjusted under 35 U.S.C. 154(b) by 133 days.

(21) Appl. No.: 13/147,249

(22) PCT Filed: Feb. 3, 2010

(86) PCT No.: PCT/JP2010/051540
§ 371 (c)(1),
(2), (4) Date: Aug. 1, 2011

(87) PCT Pub. No.: WO2010/090236
PCT Pub. Date: Aug. 12, 2010

(65) Prior Publication Data
US 2011/0288038 A1   Nov. 24, 2011

(30) Foreign Application Priority Data

Feb. 3, 2009  (JP) ................................. 2009-023016

(51) Int. Cl.
*A61K 31/70* (2006.01)
(52) U.S. Cl.
USPC ............................................ 514/27; 514/53
(58) Field of Classification Search
USPC ......................................... 514/27, 53; 536/8
See application file for complete search history.

(56) References Cited

U.S. PATENT DOCUMENTS

| 4,525,343 | A | 6/1985 | Raaf |
| 4,559,224 | A | 12/1985 | Raaf |
| 5,885,969 | A | 3/1999 | Miyake et al. |
| 2006/0153936 | A1 | 7/2006 | Tsuzaki |

FOREIGN PATENT DOCUMENTS

| EP | 0 123 296 | 10/1984 |
| JP | 62-51613 | 3/1987 |
| JP | 8-80177 | 3/1996 |
| JP | 9-71773 | 3/1997 |
| JP | 10-70994 | 3/1998 |
| JP | 10-101705 | 4/1998 |
| JP | 11-199499 | 7/1999 |
| JP | 11-346792 | 12/1999 |
| JP | 2000-236856 | 9/2000 |
| JP | 2003-12703 | 1/2003 |
| JP | 2003-284525 | 10/2003 |
| JP | 2005/003112 | 1/2005 |
| JP | 2005-132793 | 5/2005 |
| JP | 2005-162633 | 6/2005 |
| JP | 2006-241004 | 9/2006 |
| JP | 2006-249045 | 9/2006 |
| JP | 2007-091693 | 4/2007 |
| JP | 2007-308414 | 11/2007 |
| JP | 2009-013092 | 1/2009 |
| JP | 2009-029749 | 2/2009 |
| JP | 2009-084240 | 4/2009 |
| JP | 2009-256341 | 11/2009 |
| JP | 2011-73970 | 4/2011 |
| WO | 85/04106 | 9/1985 |
| WO | 02/092028 | 11/2002 |
| WO | 2008/009958 | 1/2008 |

OTHER PUBLICATIONS

International Search Report issued May 11, 2010 in International (PCT) Application No. PCT/JP2010/051540.
Supplementary European Search Report issued Jul. 31, 2012 in corresponding European Patent Application No. 10738567.6.
"Rite Aid Whole Source Mature Adult Multivitamin/Mineral", Dietary Supplements Labels Database, Jul. 23, 2004, pp. 1-2.
Kanaze et al., "Dissolution Enhancement of Flavonoids by Solid Dispersion in PVP and PEG Matrixes: A Comparative Study", Journal of Applied Polymer Science, vol. 102, 2006, pp. 460-471.
Majumdar et al., "Solubility, Stability, Physicochemical Characteristics and in Vitro Ocular Tissue Permeability of Hesperidin: A Natural Bioflavonoid", Pharmaceutical Research, vol. 26, No. 5, 2008, pp. 1217-1225.
S. Sekine et al., Cosmetic Handbook (with English translation), p. 347, Published Nov. 1, 1996.

*Primary Examiner* — Elli Peselev
(74) *Attorney, Agent, or Firm* — Wenderoth, Lind & Ponack, L.L.P.

(57) ABSTRACT

This invention relates to a composition that stably contains hesperidin. The present invention provides a composition containing (A) hesperidin, (B) at least one dihydric alcohol selected from the group consisting of ethylene glycol, diethylene glycol, triethylene glycol, polyethylene glycol, propylene glycol, dipropylene glycol, 1,3-butylene glycol, and 3-methyl-1,3-butanediol, and (C) a sugar alcohol. In the composition, the decomposition of hesperidin is suppressed and hesperidin is stably contained.

10 Claims, No Drawings

HESPERIDIN-CONTAINING COMPOSITION

TECHNICAL FIELD

The present invention relates to a composition that stably comprises hesperidin. More specifically, the present invention relates to a composition containing hesperidin, a specific dihydric alcohol, and a sugar alcohol.

BACKGROUND ART

Hesperidin is a substance having the following chemical structure:

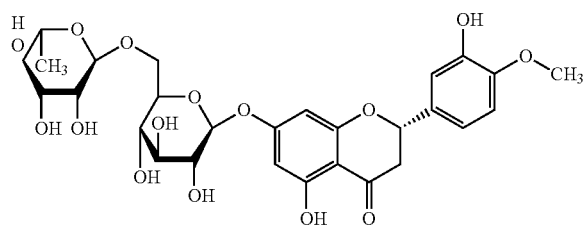

It is reported that hesperidin has effects of strengthening capillaries to reduce blood vessel permeability, effects of improving blood cholesterol and blood flow, antiallergic effects, cancer inhibition effects, etc. It is known that such excellent effects can be obtained, for example, when hesperidin is applied or orally taken.

However, hesperidin is extremely unstable in hesperidin-containing compositions, and gradually decomposes in the compositions.

Further, hesperidin is a substance with very low solubility; although it dissolves in strong alkali solutions having a pH of 11 or more, it barely dissolves in neutral to acidic solutions. For this reason, it is very difficult to obtain non-strong alkali solutions containing dissolved hesperidin to use them as foods, drugs, etc.; or use them for producing foods, drugs, etc. Furthermore, even when hesperidin is dissolved in a strong alkali solution, it is unstable and decomposed during long (e.g., several weeks) storage. Thus, hesperidin has very low stability.

An oral composition containing hesperidin is particularly expected to have an effect of maintaining the health of oral tissues by promoting the blood flow of the oral tissues; however, since the use of strong alkali solutions or strong alkali substances in the mouth damages oral tissues, it is difficult to produce and provide oral compositions that stably contain hesperidin on an industrial scale.

Under such circumstances, studies have been made to improve the stability of hesperidin in hesperidin-containing compositions. Various attempts have been made to increase the solubility of hesperidin in slightly alkaline to acidic solutions (for example, solutions having a pH of about 3 to 10).

For example, there are reports on a method comprising combining D-glucose with hesperidin to form α-glycosyl hesperidin, thereby increasing the solubility of hesperidin, and a method comprising forming an amorphous composition that contains hesperidin and a glucose adduct of hesperidin (in which glucose is attached to hesperidin) at a specific ratio, thereby improving the water solubility of hesperidin (Patent Literatures 1 and 2). However, production of glucose adducts of hesperidin is expensive; there is a problem in view of cost.

There are also reports on a method comprising dissolving hesperidin in a strong alkali solution, and then adding a polysaccharide thickener thereto to adjust the pH of the solution (Patent Literature 3). However, this method has a problem in view of stability, because hesperidin is extremely unstable, especially against light and oxygen in the alkali pH range, and impurities and crystals are gradually deposited when the pH is returned to a neutral level. Further, even when hesperidin is dissolved in strong alkali, there is a problem of decomposition during storage.

Therefore, it has been difficult thus far to suppress the decomposition of hesperidin in hesperidin-containing compositions. In particular, suppressing the decomposition of hesperidin and stably containing hesperidin in non-strong alkali solutions (e.g., solutions having a pH about 3 to 10) without using glucose adducts of hesperidin are difficult, and dissolving hesperidin is also difficult. For this reason, it is difficult to produce and supply hesperidin-containing compositions on an industrial scale.

CITATION LIST

Patent Literatures

PTL 1: Japanese Unexamined Patent Publication No. H11-346792
PTL 2: Japanese Unexamined Patent Publication No. 2007-308414
PTL 3: Japanese Unexamined Patent Publication No. H10-101705

SUMMARY OF INVENTION

Technical Problem

An object of the present invention is to provide a hesperidin composition that stably contains hesperidin.

Solution to Problem

The present inventors surprisingly found that in a composition containing hesperidin, a specific dihydric alcohol, and a sugar alcohol, the decomposition of hesperidin is suppressed and the composition stably contains hesperidin. The inventors also found that when a solution contains hesperidin, a specific dihydric alcohol, and a sugar alcohol, hesperidin can be stably dissolved in the solution that is not a strong alkali solution (solution having a pH of less than 11). With further improvement based on these findings, the inventors achieved the present invention.

Specifically, the present invention relates to compositions in the following Items.

1. A composition comprising (A) hesperidin, (B) at least one dihydric alcohol selected from the group consisting of ethylene glycol, diethylene glycol, triethylene glycol, polyethylene glycol, propylene glycol, dipropylene glycol, 1,3-butylene glycol, and 3-methyl-1,3-butanediol, and (C) a sugar alcohol.
2. The composition according to Item 1, wherein the (C) sugar alcohol is at least one member selected from the group consisting of reducing paratinose, xylitol, sorbitol, maltitol, and erythritol.
3. The composition according to Item 1 or 2, wherein the (B) dihydric alcohol is at least one member selected from the group consisting of polyethylene glycol and propylene glycol.
4. The composition according to any one of Items 1 to 3, wherein the composition is a liquid composition in which (A), (B), and (C) are dissolved.

5. The composition according to Item 4, the composition having a pH of 3 to 10.
6. The composition according to any one of Items 1 to 5, wherein the composition is an oral composition.

Advantageous Effects of Invention

According to the present invention, the decomposition of hesperidin is suppressed and a composition that stably contains hesperidin can be provided. Further, the present invention can provide a composition in which hesperidin is stably dissolved in a non-strong alkali solution (having a pH of less than 11). That is, according to the present invention, a hesperidin composition (e.g., liquid composition or gel composition) in which hesperidin is dissolved in a solution having a pH of less than 11 can be obtained. In the hesperidin composition, the decomposition of the hesperidin is suppressed, and a decrease in the hesperidin content in the composition can be reduced.

The hesperidin composition can be used as a pharmaceutical composition, food composition, and oral composition without any treatment. Further, the hesperidin composition can be used for producing pharmaceutical compositions, food compositions, and oral compositions, each stably containing hesperidin, in an easy manner.

DETAILED DESCRIPTION OF THE INVENTION

The present invention is explained in detail below.

The present invention relates to a hesperidin composition comprising hesperidin, a specific dihydric alcohol, and a sugar alcohol.

As the hesperidin contained in the hesperidin composition of the present invention, hesperidin extracted from citrus peel by a known method can be used. Hesperidin can also be purchased from Wako Pure Chemical Industries, Ltd., Hamari Chemicals, Ltd., Alps Pharmaceutical Ind. Co., Ltd., etc. Crude hesperidin, i.e., hesperidin that is being refined from material such as citrus peel, can be used in place of purified hesperidin.

The specific dihydric alcohol used in the present invention is ethylene glycol, diethylene glycol, triethylene glycol, polyethylene glycol, propylene glycol, dipropylene glycol, 1,3-butylene glycol, polybutylene glycol, or 3-methyl-1,3-butanediol. Of these, polyethylene glycol (PEG) and propylene glycol (PG) are preferred. The dihydric alcohols may be used alone or in a combination of two or more.

The PEG used in the present invention is not particularly limited; however, PEG preferably has a weight average molecular weight of about 2,000 or less, more preferably about 200 to 1,500, and even more preferably about 400 to 1,500. The weight average molecular weight is a value obtained using a matrix-assisted laser desorption/ionization time-of-flight mass spectrometry.

The sugar alcohol used in the present invention is not particularly limited. Examples of preferable sugar alcohols include paratinose, reducing paratinose, xylitol, sorbitol, maltitol, erythritol, trehalose, lactitol, etc. Of these, reducing paratinose, xylitol, sorbitol, maltitol, and erythritol are particularly preferred. The sugar alcohols can be used alone or in a combination of two or more.

Since the hesperidin composition of the present invention contains hesperidin, a specific dihydric alcohol, and a sugar alcohol, the decomposition of the hesperidin is suppressed and the hesperidin can be stably contained in the composition.

The amount of hesperidin in the hesperidin composition of the present invention is not particularly limited, but it is generally about 0.0001 to 0.3 wt %, preferably 0.0001 to 0.1 wt %, more preferably 0.001 to 0.1 wt %, even more preferably 0.001 to 0.05 wt %, and still more preferably 0.001 to 0.01 wt %. The amount of dihydric alcohol is preferably 1 to 10 wt %, and more preferably about 2 to 6 wt % based on the composition. The amount of sugar alcohol is preferably 1 to 30 wt %, more preferably 1 to 20 wt %, and even more preferably 5 to 15 wt % based on the composition.

In the hesperidin composition of the present invention, the amount of dihydric alcohol is preferably 30 to 34,000 parts by weight, more preferably 50 to 7,500 parts by weight, and even more preferably about 100 to 4,000 parts by weight per part by weight of hesperidin. The amount of sugar alcohol is preferably 50 to 13,000 parts by weight, more preferably 50 to 10,000 parts by weight, and even more preferably about 100 to 5,000 parts by weight per part by weight of hesperidin.

In the hesperidin composition of the present invention, when the sugar alcohol is contained in an amount of 10 parts by weight, the dihydric alcohol is preferably contained in an amount of 3 to 10 parts by weight, and more preferably 4 to 9 parts by weight.

There is no particular limitation on the forms of the hesperidin composition of the present invention, but hesperidin-containing liquid compositions or hesperidin-containing gel compositions are preferable (slightly alkali to slightly acid liquid compositions having a pH of 10 or less are more preferable). Of liquid compositions, water-soluble compositions are preferable. The hesperidin composition generally has a pH of 3 to 10, preferably 4 to 9, and more preferably 5 to 8. Herein, the pH value is measured at 25° C. using a pH meter. Compositions whose pHs are measurable by a pH meter are referred to as liquid compositions, even when the compositions have viscosity.

In addition to hesperidin, a specific dihydric alcohol, and a sugar alcohol, the hesperidin composition of the present invention may contain optional components as long as the effects of the present invention (particularly, hesperidin stability in the composition) are not impaired.

The hesperidin composition of the present invention can be produced by suitably mixing hesperidin, a specific dihydric alcohol, a sugar alcohol, and, if necessary, optional components, with a solvent. As a solvent, water is preferred.

The hesperidin composition of the present invention can be preferably used as a food composition, pharmaceutical composition, cosmetic composition, or oral composition; and more preferably, a food composition, pharmaceutical composition, or oral composition.

In addition to the effects of strengthening capillaries to reduce blood vessel permeability, effects of improving blood cholesterol and blood flow, antiallergic effects, and cancer inhibition effects, as mentioned above, hesperidin has significant anti-caries effects (in particular, effects of preventing dentine caries). Accordingly, the composition that stably contains hesperidin is particularly preferably used as a food composition, pharmaceutical composition, or oral composition for attaining such effects. Of these, the composition is more preferably used as an anti-caries food composition, anti-caries pharmaceutical composition, or anti-caries oral composition.

When the hesperidin composition of the present invention is used as a pharmaceutical composition, if necessary, pharmacologically active components other than hesperidin, pharmacologically acceptable base agents, carriers, additives (e.g., solvents, dispersants, emulsifiers, buffers, stabilizers, excipients, binders, disintegrants, and lubricants) can be added as optional components insofar as the composition (hereinafter, sometimes referred to as "the pharmaceutical composition of the present invention") does not impair the effects of the present invention (hesperidin stability in the composition).

The pharmaceutical composition of the present invention may be formed into pharmaceutical formulations such as tablets, pills, powders, solutions, suspensions, emulsions, granules, and capsules. Of these, the pharmaceutical composition of the present invention is preferably formed into pharmaceutical products used in the mouth, particularly, intraoral agents, topical liniments, and solutions. In particular, such pharmaceutical compositions of the present invention are administered orally for use.

The dose of the pharmaceutical composition of the present invention can be suitably determined. The pharmaceutical composition of the present invention may be administered to hypercholesterolemia patients, allergic disease patients (for example, atopic dermatitis patients), cancer patients, patients at high risk of developing dentine caries, individuals who are unable to provide self-oral care, periodontal disease patients, etc.

When the hesperidin composition of the present invention is used as a food composition, base agents, carriers, and additives that are food hygienically acceptable, as well as components and materials that are usable as foods can be suitably added as optional components insofar as the composition (hereinafter, sometimes referred to as "the food composition of the present invention") does not impair the effects of the present invention (hesperidin stability in the composition). By adding such optional components, the food composition of the present invention can be used as a processed food, beverage, health food (food with nutrient function claims or food for specified health use), supplement, food for the sick (hospital food, patient food, or nursing food, etc. The optional components can also be added to food or beverage products such as snacks (e.g., chewing gums, chocolates, candies, tablets, biscuits, cookies, okaki and sembei (types of rice crackers), puddings, and almond jelly), bread, soups (including powdered soups), and processed foods.

When the composition is used as a health food (food with nutrient function claims or food for specified health use) or a supplement, the composition is preferably made into forms such as chewing gums, candies, granules, capsules, tablets (including chewable tablets), and beverages (drink preparations) in view of ease of continuous intake. Of these, chewing gums, candies, capsules, tablets (including chewable tablets) are preferable in view of the convenience of administration. In particular, chewing gums, candies, and tablets held for a prolonged time in the mouth are preferable. The food compositions of the present invention in these forms can be suitably prepared according to ordinal methods using carriers, etc., that are pharmaceutically acceptable and/or food hygienically acceptable.

The dose and the subject of the food composition of the present invention are not particularly limited; preferably, however, they are the same as those described in the pharmaceutical composition of the present invention.

Note that hospital food is meals offered during hospitalization, patient food is meals for the sick, and nursing food is meals for care receivers.

When the hesperidin composition of the present invention is used as an oral composition, the composition (hereinafter referred to as "the oral composition of the present invention") can be formed into external compositions, such as dentifrices (toothpastes, tooth liquids, and liquid dentifrices), mouthwashes, spray formulations, liniments, varnish formulations, foaming agents, creams, pastas, gels, patches, external dispersed pastes, and liquid external preparations, and internal compositions such as solutions, syrups, and dry syrups. Of these, gel agents, liquid preparations, and preparations easily produced with liquids are preferable; and liquid dentifrices, mouthwashes, and liniments are more preferable.

Optional components shown below can be suitably added to the oral composition of the present invention in such a manner that suits the forms of the composition, insofar as they do not impair the effects of the present invention.

For example, as surfactants, nonionic surfactants, amphoteric surfactants, anionic surfactants, cationic surfactants, etc., can be added. Examples of the nonionic surfactants include glycerol fatty acid esters, sucrose fatty acid esters, sorbitan fatty acid esters, polyoxyethylene fatty acid esters, fatty acid diethanolamides, etc. Examples of amphoteric surfactants include betaine-type amphoteric surfactants, imidazolinium betaine-type amphoteric surfactant, etc. Examples of anionic surfactants include alkyl sulfate salts, alkyl ether sulfate salts, alkylbenzene sulfonate salts, N-acylamino acid salts, etc. Examples of cationic surfactants include alkyl ammonium salt-type cationic surfactants, alkyl benzylammonium salt-type cationic surfactants, amino acid-based surfactants, etc. These surfactants can be used alone or in a combination of two or more.

Examples of flavoring agents (flavorings) include menthol, carboxylic acid, anethole, eugenol, methyl salicylate, limonene, methyl acetate, methyleugenol, cineole, linalool, thymol, spearmint oil, peppe/mint oil, lemon oil, orange oil, sage oil, rosemary oil, cinnamon oil, perilla oil, wintergreen oil, clove oil, eucalyptus oil, pimento oil, etc. These flavoring agents can be used alone or in a combination of two or more.

Examples of sweetening agents include sodium saccharin, acesulfame potassium, stevioside, glycyrrhizin, glycerol, etc. These sweetening agents can be used alone or in a combination of two or more.

To impart viscosity that does not impair the pleasant feeling of use to the oral composition, a thickener, for example, can be used. Examples of thickeners include methyl cellulose, ethyl cellulose, sodium carboxymethylcellulose, carboxy methyl ethyl cellulose, hydroxyethylcellulose, hydroxypropylcellulose, hydroxypropylmethylcellulose, sodium alginate, xanthan gum, tragacanth gum, karaya gum, gum arabic, veegum, carrageenan, polyvinyl alcohol, sodium polyacrylate, carboxyvinyl polymer, polyvinyl pyrrolidone, silica gel, shellac, methacrylic acid copolymer, ethyl acrylate and methacrylate copolymer dispersion, amino alkyl methacrylic acid copolymer, hydroxypropylmethylcellulose phthalate, hydroxypropylmethylcellulose acetate succinate, zein, polyvinyl acetal diethylamino acetate, mixtures of fumaric acid, stearic acid, polyvinyl acetal diethylamino acetate, and hydroxypropylmethylcellulose 2910, etc. Such thickeners can be used alone or in a combination of two or more. Some of the thickeners can be used as a gelling agent, and can be used for gellation. When a thickener used as a gelling agent requires ion as a gelling aid, a suitable gelling aid can be added in combination. For example, when sodium alginate is used as a gelling agent, calcium chloride can be used as a gelling aid; and when carrageenan is used as a gelling agent, calcium lactate can be used as a gelling aid.

As pharmaceutically effective components, examples include cationic bactericides such as cetylpyridinium chloride, chlorhexidine hydrochloride, and benzethonium chloride; vitamin E such as acetic acid dl-a-tocopherol, succinic acid tocopherol, and nicotinic acid tocopherol; nonionic disinfectants such as triclosan and isopropylmethyl phenol; enzymes such as dextranase, protease, mutanase, lysozyme, and lytic enzyme; tranexamic acid; epsilon aminocaproic acid; allantoin; glycyrrhizin salts (for example, dipotassium glycyrrhizinate); glycyrrhetic acid; chlorophyll; sodium chloride; alkali metal monofluorophosphates such as sodium monofluorophosphate and potassium monofluorophosphate; fluorides such as sodium fluoride and stannous fluoride; caropeptide; allantoin; carbazochrome; hinokitiol; potassium nitrate; etc. Such pharmaceutically effective components can be used alone or in a combination of two or more.

As an abrasive, dicalcium phosphate dihydrate, dicalcium phosphate anhydrous, calcium phosphate, tricalcium phosphate, calcium carbonate, calcium pyrophosphate, aluminium hydroxide, alumina, anhydrous silicic acid, silica gel, aluminium silicate, insoluble sodium metaphosphate, trimagnesium phosphate, magnesium carbonate, calcium sulfate, polymethylmethacrylate, bentonite, zirconium silicate, hydroxyapatite, synthetic resin, etc. These abrasives can be used alone or in a combination of two or more.

Examples of usable preservatives include methylparaben, ethylparaben, propylparaben, butylparaben, and other parabens; sodium benzoate, phenoxyethanol, alkyldiaminoethylglycine hydrochloride, etc. These can be used alone or in a combination of two or more.

Examples of usable colorants include legal colors, such as Blue No. 1, Yellow No. 4, Red No. 202, and Green No. 3; mineral-based pigments, such as ultramarine blue, deep ultramarine blue, and Prussian blue; titanium oxide; etc. These can be used alone or in a combination of two or more.

In addition, any components that can generally be mixed with oral compositions may be added as optional components. Among such optional components, those that can suitably be added to food may be added, as appropriate, to the food composition of the present invention.

Among the hesperidin compositions of the present invention, the liquid composition (preferably having a pH of 3 to 10) in particular, in which hesperidin is stably dissolved, can be prepared, for example, in the following manner. First, hesperidin is dissolved in an alkaline solution (for example, having a pH of 11 or more), and the pH is adjusted. A specific dihydric alcohol and a sugar alcohol may then be dissolved in this solution. Alternatively, for example, hesperidin, a dihydric alcohol, and a sugar alcohol may be dissolved in an alkaline solution, and the pH of the resulting solution may be adjusted. Dissolving the above-mentioned amounts of dihydric alcohol and sugar alcohol prevents problems, such as formation of cloudiness and deposition of crystals, when the pH is returned to near-neutral. Furthermore, the decomposition of hesperidin in the composition can be inhibited. Thus, hesperidin is very stably dissolved in the liquid composition comprising the hesperidin, specific dihydric alcohol, and sugar alcohol in a dissolved state. For example, when the liquid composition is directly used as a food composition, pharmaceutical composition, or oral composition, it is preferable to dissolve hesperidin in an alkaline solution, and then adjust the pH of the resulting solution to generally 3 to 10, preferably 4 to 9, and more preferably 5 to 8, using a pH adjuster.

The present invention also provides a method for producing a liquid composition in which hesperidin is stably dissolved. That is, the present invention provides a method for producing a liquid composition (generally having a pH of 3 to 10, preferably 4 to 9, and more preferably 5 to 8) in which hesperidin is dissolved, the method comprising the step of dissolving hesperidin, a specific dihydric alcohol, and a sugar alcohol in a solvent (preferably water or aqueous solution). More specifically, the present invention provides a method for producing a liquid composition comprising hesperidin in a dissolved state, the method comprising the four steps of:

(α) dissolving hesperidin in an alkaline solution (preferably having a pH of 11 or more);
(β) dissolving a dihydric alcohol in the solution;
(γ) dissolving a sugar alcohol in the solution; and
(δ) adjusting the pH of the solution to 3 to 10, preferably 4 to 9, and more preferably 5 to 8.

The order of performing steps (α) to (δ) is not limited, as long as step (α) is followed by step (δ). Moreover, among steps (α) to (γ), two or three steps may be performed simultaneously. Among steps (α) to (δ), it is preferable to perform step (α) first. When the pH of the solution is 3 to 10, preferably 4 to 9, and more preferably 5 to 8, after steps (α) to (γ) are completed, step (δ) can be omitted.

Examples of usable alkaline solutions include solutions of sodium hydroxide, potassium hydroxide, calcium hydroxide, ammonia, disodium hydrogenphosphate anhydride, disodium hydrogenphosphate dodecahydrate, trisodium phosphate dodecahydrate, sodium acetate trihydrate, calcium lactate pentahydrate, sodium hydrogen carbonate anhydride, sodium carbonate, potassium carbonate, or the like. More preferable is a solution of sodium hydroxide or sodium carbonate, and the most preferable is a sodium carbonate solution. These solutions can be used alone or in a combination of two or more. It is preferable that these solutions be aqueous solutions. The pH of these solutions is preferably 11 or more, although the pH is not limited as long as hesperidin can be dissolved.

Examples of pH adjusters include inorganic acids, such as hydrochloric acid, sulfuric acid, carbonic acid, and phosphoric acid; and organic acids, such as citric acid, malic acid, adipic acid, fumaric acid, maleic acid, succinic acid, pyruvic acid, gluconic acid, tartaric acid, formic acid, acetic acid, lactic acid, and salts thereof. Preferable among them is citric acid. These pH adjusters can be used alone or in a combination of two or more.

Moreover, the liquid composition stably comprising hesperidin can suitably contain optional components, for example, those described above, as long as the effects of the present invention (particularly the stability and solubility of hesperidin in the composition) are not impaired.

The thus-obtained liquid composition in which hesperidin is stably dissolved can be suitably used directly as, for example, a food composition, pharmaceutical composition, oral composition, or the like. The liquid composition can also be suitably used in the production of food, pharmaceuticals (food compositions and pharmaceutical compositions), etc. Additionally, the liquid composition can be suitably used in the production of oral compositions. The use of the liquid composition in which hesperidin is stably dissolved significantly improves the workability during the production of these compositions.

In this specification, the phrase "the hesperidin composition stably comprising hesperidin" indicates that the decomposition of hesperidin is inhibited in the composition, and that the hesperidin content in the composition after long-term storage is not significantly changed from the hesperidin content in the composition immediately after production. Specifically, it is preferable that the hesperidin content does not decrease even at a storage temperature ranging from a low temperature to a high temperature (e.g., 5 to 55° C.). For example, it is preferable that the decrease rate of hesperidin content be 30% or less when the composition is stored at 5 to 55° C. for three weeks after production. Moreover, it is more preferable that the decrease rate of hesperidin content be 10% or less when the composition satisfies these conditions and is stored at 5° C. for three weeks after production.

The decrease rate of hesperidin content can be determined by, for example, analyzing the composition by high-performance liquid chromatography (HPLC) immediately after production and after storage, and comparing the hesperidin content in the composition immediately after production with the hesperidin content in the composition after storage. In the HPLC analysis, the composition comprising hesperidin may be analyzed after filtering. A filter having a pore size of 0.45% μm may be used. Moreover, the composition may be diluted with, for example, a suitable dilution before filtering. Such a dilution may be, for example, water, alcohol, or a mixture of water and alcohol. Specifically, for example, a mixture of methanol and water (weight ratio=1:1) can be used.

EXAMPLES

The present invention is described in detail below; however, the present invention is not limited to the following examples.

Production Example 1

Liquid compositions comprising hesperidin in a dissolved state were produced in each example according to the following procedure.

First, 40 mg of hesperidin (Wako Pure Chemical Industries, Ltd.) was dissolved in about 180 mL of 0.05 M sodium carbonate aqueous solution. An anhydrous citric acid aqueous solution was added thereto, and the pH was adjusted to 7.0. The mixture was diluted to 200 mL with distilled water to prepare a hesperidin solution.

Next, 10 mL of the hesperidin solution prepared in the above manner was added to a 100-mL volumetric flask in which about 50 mL of distilled water and an additive shown in Table 1 had been placed. The mixture was diluted to 100 mL with distilled water, thereby preparing compositions of Examples #1 to #7 and compositions of Comparative Examples #8 to #15. The amounts of hesperidin and additives shown in Table 1 are represented by wt % in each composition.

Additionally, compositions to which polyoxyethylene (60) hydrogenated castor oil (HCO-60) had been added as an additive were also examined. HCO-60 is a surfactant commonly used in food production, etc., and this examination is intended to investigate if such a surfactant contributes to enhancing the solubility of hesperidin.

All of the compositions thus obtained in Examples #1 to #7 and Comparative Examples #8 to #15 had a pH of 7.

Stability Test 1

Each of the compositions of the Examples and Comparative Examples (80 mL) prepared in the above production example was placed in a transparent bottle, and allowed to stand at 5° C. or 55° C. for three weeks in a dark room. Separately, each of the compositions of the Examples and Comparative Examples was filtered through a filter immediately after preparation, followed by HPLC analysis, and a peak indicating hesperidin was measured in each example. The peak is regarded as the "peak immediately after production".

The bottles were further allowed to stand in a dark room. Then, the solution of each bottle was filtered through a filter, followed by HPLC analysis, and a peak indicating hesperidin was measured in each component.

The proportion of the area of this peak to the area of the "peak immediately after production", which was regarded as 100%, was examined for each composition. The results are shown in the "Stability" column of Table 1. The peak area indicates the amount of hesperidin dissolved in each composition solution. A higher peak area (%) implies that hesperidin does not precipitate or decompose, and is stably dissolved.

HPLC analysis was specifically performed in such a manner that each of the example compositions and comparative example compositions was suitably diluted with a mixed solution of methanol and water (weight ratio=1:1), followed by filtration through a microfilter; and 10 μL of each solution was subjected to HPLC. The HPLC analysis conditions used in this test are as follows:

Filter
Filtration filter used: Minisart RC15 (pore size: 0.45 μm; film material: cellulose acetate) (Sartorius Mechatronics Japan)
HPLC
HPLC equipment used: LC-10AS (Shimadzu Corp.)
Detector: ultraviolet absorptiometer (measured wavelength: 284 nm)
Column: stainless pipe (inner diameter: about 5 mm, length: about 15 cm) filled with about 5 μm of octadecyl-silylated silica gel for liquid chromatography (Inertsil®, produced by GL Sciences; ODS-2: 5 μm, 4.6×150 mm)
Column temperature: constant temperature of around 40° C.
Mobile phase: 0.03 mol/L potassium dihydrogen phosphate reagent-methanol-acetonitrile mixture (7:2:1)
Flow rate: adjusted so that the retention time of hesperidin was about 10 minutes (about 1 mL/min.).

TABLE 1

| | Component | | Ex. | | | | | | | Comp. Ex. | |
| --- | --- | --- | --- | --- | --- | --- | --- | --- | --- | --- | --- |
| | | #1 | #2 | #3 | #4 | #5 | #6 | #7 | #8 | #9 |
| | Hesperidin | 0.002 | 0.002 | 0.002 | 0.002 | 0.002 | 0.002 | 0.002 | 0.002 | 0.002 |
| Additive | PEG | 4 | 4 | 4 | 4 | 4 | | | | 4 |
| | PG | | | | | | 4 | 4 | | |
| | HCO-60 | | | | | | | | | |
| | Reduced palatinose | 10 | | | | | 10 | | | |
| | Sorbitol | | 10 | | | | | | 10 | |
| | Erythritol | | | 10 | | | | | | |
| | Xylitol | | | | 10 | | | | | |
| | Maltitol | | | | | 10 | | | | |
| | Purified water | Remainder | Remainder | Remainder | Remainder | Remainder | Remainder | Remainder | Remainder | Remainder |
| Stability | 5° C. | 99.3% | 100.1% | 100.2% | 100.5% | 100.2% | 96.5% | 100.7% | 81.6% | 99.7% |
| | 55° C. | 85.0% | 73.4% | 73.2% | 73.5% | 71.9% | 80.8% | 91.1% | 64.8% | 35.5% |

TABLE 1-continued

|  | Component | Comp. Ex. | | | | | |
| --- | --- | --- | --- | --- | --- | --- | --- |
|  |  | #10 | #11 | #12 | #13 | #14 | #15 |
|  | Hesperidin | 0.002 | 0.002 | 0.002 | 0.002 | 0.002 | 0.002 |
| Additive | PEG |  |  | 4 | 4 |  |  |
|  | PG | 4 |  | 4 |  | 4 |  |
|  | HCO-60 |  |  |  | 0.3 | 0.3 | 0.3 |
|  | Reduced palatinose |  | 10 |  |  |  | 10 |
|  | Sorbitol |  |  |  |  |  |  |
|  | Erythritol |  |  |  |  |  |  |
|  | Xylitol |  |  |  |  |  |  |
|  | Maltitol |  |  |  |  |  |  |
|  | Purified water | Remainder | Remainder | Remainder | Remainder | Remainder | Remainder |
| Stability | 5° C. | 100.1% | 97.0% | 81.6% | 94.4% | 73.1% | 85.2% |
|  | 55° C. | 46.0% | 62.5% | 38.5% | 21.5% | 58.7% | 57.6% |

PEG: polyethylene glycol
PG: propylene glycol
HCO-60: Polyoxyethylene (60) hydrogenated castor oil Table 1 reveals that the hesperidin compositions to which either or neither of dihydric alcohol and sugar alcohol was added (Comparative Examples) all showed a remarkable decrease in the hesperidin content, particularly after storage at 55° C., from immediately after production; and were unstable.

In contrast, as for the hesperidin compositions comprising a dihydric alcohol and a sugar alcohol (Examples), it was demonstrated that the hesperidin content after storage at 5° C. was almost equivalent to that immediately after production, and that the hesperidin content after storage at 55° C. was at least 70% or more relative to that immediately after production.

The above results continued that the stability of hesperidin cannot be enhanced without the addition of both dihydric alcohol and sugar alcohol.

In addition, the results of Comparative Examples #9 to #11 and #13 to #15 suggested that HCO-60 did not function to enhance the stability of hesperidin.

Production Example 2

The components shown in Table 2 were mixed to produce compositions (Examples #16 and #17, and Comparative Examples #18 and #19). In Comparative Examples #18 and #19, each composition was produced by mixing all of the components shown in Table 2 at once. However, in Comparative Examples #18, a 0.05 M sodium carbonate aqueous solution was used in place of purified water. The compositions of Examples #16 and #17 were produced as follows:

(i) Intermediate Product 1: Xanthan gum and sodium carboxymethylcellulose were gradually added to glycerin while stirring to form a homogeneous mixture.

(ii) Intermediate Product 2: Water-soluble components (reduced palatinose, sodium fluoride, and potassium nitrate) and hesperidin were sequentially added to purified water, and the mixture was stirred to form a homogeneous mixture.

(iii) Intermediate Product 2 was added to Intermediate Product 1 while stirring, and the mixture was further stirred to for a homogenous mixture.

(iv) After further adding sorbitol, the remaining components were added and stirred to foam a homogenous mixture, followed by defoaming, thereby obtaining a hesperidin-containing composition.

The compositions of Examples #16, #17, and #19 were highly viscous liquid compositions because they contained thickening agents (sodium carboxymethylcellulose and xanthan gum). Hesperidin was considered to be uniformly dispersed in these compositions.

Stability Test 2

The compositions of Examples #16 and #17, and the compositions of Comparative Examples #18 and #19 were analyzed by HPLC in the same manner as in Stability Test 1. Additionally, standard solutions for preparing the calibration curve were prepared, and were similarly subjected to HPLC analysis. The calibration curve was prepared by plotting hesperidin concentrations (mg/L) on a horizontal axis, and peak areas (μV·sec) corresponding to each hesperidin concentration on a vertical axis. Subsequently, the hesperidin concentration (mg/L) of each of the solutions of Examples and Comparative Examples was determined from the peak area (μV·sec) of each solution measured in the Examples and Comparative Examples, using the linear regression equation of the calibration curve. The standard solutions for preparing the calibration curve were obtained by dissolving hesperidin in methanol by ultrasonic irradiation. These solutions were sequentially diluted, and used to prepare the calibration curve.

Furthermore, the resulting hesperidin concentration was used to determine the rate of the hesperidin content in each composition after three-week storage (at 5° C., or 55° C.) to the hesperidin content in each composition immediately after production, which was regarded as 100%. The results are shown in the "Stability" column of Table 2. Table 2 also shows the pH of each composition.

TABLE 2

|  | Ex. | | Comp Ex. | |
| --- | --- | --- | --- | --- |
|  | #16 | #17 | #18 | #19 |
| Hesperidin | 0.1 | 0.1 | 0.02 | 0.1 |
| PEG |  |  |  |  |
| PG | 3 | 3 |  |  |
| HCO-60 | 0.4 | 0.4 |  |  |
| Reduced palatinose | 10 | 10 |  | 10 |
| Sorbitol | 10 | 20 |  | 10 |
| Glycerin | 15 | 10 |  |  |
| CMC-Na | 2 | 3 |  | 3 |
| Xanthane gum | 0.5 |  |  |  |
| Sodium fluoride | 0.2 | 0.2 |  |  |
| Potassium nitrate | 5 | 5 |  |  |
| Flavor | 0.3 | 0.3 |  |  |

TABLE 2-continued

|  | Ex. | | Comp Ex. | |
| --- | --- | --- | --- | --- |
|  | #16 | #17 | #18 | #19 |
| Disodium monohydrogen phosphate | 0.25 | 0.25 | | |
| Sodium dihydrogen phosphate | 0.04 | 0.04 | | |
| Methyl parabenzoate | 0.2 | 0.2 | | |
| Purified water* | Remainder | Remainder | Remainder | Remainder |
| pH | 6.6 | 6.6 | 11 | 6.8 |
| Stability 5° C. | 96.0% | 94.8% | 61.5% | 95.1% |
| 55° C. | 87.4% | 83.1% | 20.3% | 68.6% |

*A 0.05M sodium carbonate solution was used in place of purified water only in Example #18.

A comparison of the compositions #16, #17, and #19 confirmed that the viscous liquid compositions comprising hesperidin in a dispersed state can inhibit the decomposition of hesperidin, and stably contain hesperidin, because they comprise a specific dihydric alcohol and a sugar alcohol.

In addition, the results of the composition #18 suggested that hesperidin was easily dissolved in an alkaline solution, but showed poor stability after being dissolved.

The following shows formulation examples of the oral composition of the present invention. Each amount is represented by wt %.

Formulation Example 1

Liniment

| Component | Amount |
| --- | --- |
| Shellac | 10.0 |
| Sorbitol | 10.0 |
| Ethyl alcohol | 40.0 |
| Polyethylene glycol | 4.0 |
| Sodium carbonate | 0.2 |
| Hesperidin | 0.002 |
| Flavor | 1.5 |
| Citric acid | suitable amount |
| Purified water | remainder |
| Total | 100.0 |

Formulation Example 2

Mouthwash

| Component | Amount |
| --- | --- |
| Ethanol | 10.0 |
| Reduced palatinose | 10.0 |
| Polyethylene glycol | 3.0 |
| Glycerin | 5.0 |
| Sodium carbonate | 0.2 |
| Sodium citrate | 0.1 |
| Methyl parahydroxybenzoate | 0.1 |
| Vitamin E | 0.05 |
| Vitamin C | 0.01 |
| Hesperidin | 0.002 |
| Flavor | 0.2 |
| Citric acid | suitable amount |
| Purified water | remainder |
| Total | 100.0 |

Formulation Example 3

Gel for Oral Cavity

| Component | Amount |
| --- | --- |
| Glycerin | 30.0 |
| Sorbitol | 13.0 |
| Propylene glycol | 4.0 |
| Carboxymethylcellulose | 0.2 |
| Vitamin E | 0.05 |
| Hesperidin | 0.001 |
| Flavor | 0.2 |
| Sodium hydroxide | suitable amount |
| Citric acid | suitable amount |
| Purified water | remainder |
| Total | 100.0 |

Formulation Example 4

Mouse Spray

| Component | Amount |
| --- | --- |
| Glycerin | 10.0 |
| Reduced palatinose | 5.0 |
| Ethanol | 10.0 |
| Trehalose | 5.0 |
| Polyethylene glycol | 5.0 |
| Cetylpyridinium chloride | 0.3 |
| Stevia extract | 0.1 |
| Hesperidin | 0.002 |
| Flavor | 0.2 |
| Sodium hydroxide | suitable amount |
| Citric acid | suitable amount |
| Purified water | remainder |
| Total | 100.0 |

Formulation Example 5

Dentifrice

| Component | Amount |
| --- | --- |
| Reduced palatinose | 5.0 |
| Dibasic calcium phosphate/dehydrate | 20.0 |
| Carboxymethylcellulose | 3.0 |
| Potassium nitrate | 5.0 |
| Sodium fluoride | 1.05 |
| Propylene glycol | 5.0 |
| Hesperidin | 0.1 |
| Methyl parahydroxybenzoate | 0.2 |
| Polyoxyethylene hydrogenated castor oil | 0.4 |
| Flavor | 0.3 |
| Saccharine sodium | 0.1 |
| Sodium dihydrogen phosphate | suitable amount |
| Disodium hydrogen phosphate | suitable amount |
| Purified water | remainder |
| Total | 100.0 |

Formulation Example 6

Gel Dentifrice

| Component | Amount |
| --- | --- |
| Reduced palatinose | 10.0 |
| Sorbitol | 10.0 |
| Carboxymethylcellulose | 2.0 |
| Xanthane gum | 1.0 |
| Potassium nitrate | 5.0 |
| Sodium fluoride | 0.21 |
| Propylene glycol | 0.2 |
| Hesperidin | 0.002 |
| Methyl parahydroxybenzoate | 0.2 |
| Polyoxyethylene hydrogenated castor oil | 0.4 |
| Flavor | 0.3 |
| Sodium dihydrogen phosphate | suitable amount |
| Disodium hydrogen phosphate | suitable amount |
| Purified water | remainder |
| Total | 100.0 |

Formulation Example 7

Mouthwash

| Component | Amount |
| --- | --- |
| Sorbitol | 10.0 |
| Reduced palatinose | 10.0 |
| Glycerin | 1.0 |
| Calcium gluconate | 0.15 |
| Sodium monofluorophosphate | 0.7 |
| Propylene glycol | 3.0 |
| Hesperidin | 0.02 |
| Methyl parahydroxybenzoate | 0.1 |
| Polyoxyethylene hydrogenated castor oil | 0.2 |
| Flavor | 1.0 |
| Sodium hydrogen carbonate | suitable amount |
| Disodium carbonate | suitable amount |
| Purified water | remainder |
| Total | 100.0 |

Formulation Example 8

Mouthwash

| Component | Amount |
| --- | --- |
| Glycerin | 10.0 |
| Sorbitol | 10.0 |
| Sodium fluoride | 0.3 |
| Propylene glycol | 2.0 |
| Hesperidin | 0.02 |
| Methyl parahydroxybenzoate | 0.1 |
| Polyoxyethylene hydrogenated castor oil | 0.2 |
| Flavor | 0.1 |
| Glycine | suitable amount |
| Sodium hydroxide | suitable amount |
| Purified water | remainder |
| Total | 100.0 |

The invention claimed is:

1. A composition comprising:

(A) hesperidin, (B) at least one dihydric alcohol selected from the group consisting of ethylene glycol, diethylene glycol, triethylene glycol, polyethylene glycol, propylene glycol, dipropylene glycol, 1,3-butylene glycol, and 3-methyl-1,3-butanediol, and (C) a sugar alcohol, wherein:

the (A) hesperidin, (B) dihydric alcohol, and (C) sugar alcohol are dissolved in the composition, and the composition has a pH of 3-10.

2. The composition according to claim 1, wherein the (C) sugar alcohol is at least one alcohol selected from the group consisting of reducing paratinose, xylitol, sorbitol, maltitol, and erythritol.

3. The composition according to claim 1, wherein the (B) dihydric alcohol is at least one alcohol selected from the group consisting of polyethylene glycol and propylene glycol.

4. The composition according to claim 1, wherein the composition is an oral composition.

5. The composition according to claim 2, wherein the (B) dihydric alcohol is at least one alcohol selected from the group consisting of polyethylene glycol and propylene glycol.

6. The composition according to claim 2, wherein the composition is an oral composition.

7. The composition according to claim 3, wherein the composition is an oral composition.

8. The composition according to claim 1, wherein the amount of the (A) hesperidin is 0.0001 to 0.3 wt %.

9. The composition according to claim 2, wherein the amount of the (A) hesperidin is 0.0001 to 0.3 wt %.

10. The composition according to claim 3, wherein the amount of the (A) hesperidin is 0.0001 to 0.3 wt %.

* * * * *